(12) United States Patent
Oberthür

(10) Patent No.: US 7,323,520 B2
(45) Date of Patent: Jan. 29, 2008

(54) ANTI-AGING AGENTS FOR RUBBER VULCANIZATES BASED ON ORGANIC COMPOUNDS CONTAINING CONJUGATED AZADIENES

(75) Inventor: Markus Oberthür, Brunsbüttel (DE)

(73) Assignee: LANXESS Deutschland GmbH, Leverkusen (DE)

( * ) Notice: Subject to any disclaimer, the term of this patent is extended or adjusted under 35 U.S.C. 154(b) by 190 days.

(21) Appl. No.: 10/694,584

(22) Filed: Oct. 27, 2003

(65) Prior Publication Data

US 2004/0087722 A1 May 6, 2004

(30) Foreign Application Priority Data

Oct. 31, 2002 (DE) ............... 102 50 709

(51) Int. Cl.
*C08G 59/46* (2006.01)
*C08C 19/22* (2006.01)

(52) U.S. Cl. .................... 525/332.7; 525/186

(58) Field of Classification Search ............ 525/332.7, 525/186
See application file for complete search history.

(56) References Cited

U.S. PATENT DOCUMENTS 5,965,678 A * 10/1999 Becke et al. ............... 526/160
2002/0006994 A1 1/2002 Laue et al. ................ 524/241

FOREIGN PATENT DOCUMENTS

GB 1035262 7/1966

OTHER PUBLICATIONS

Ullmanns Enzyklopädie der technischen Chemie, Verlag Chemie, Weinheim, 4th edition, vol. 8, (month unavailable) 1974, pp. 19-45, Dr. Werner Kurze, Dr. F. Faschig, "Antioxidantien".

U.S Appl. No. 09/850,511, filed May 7, 2001 title: "Covulcanizable Anit-Aging Agents".

Database CA 'Online! Chemical Abstracts Service, Columbus, Ohio, US; Sumitomo Chemical Co. Ltd., Japan: "N—(1-Methylalkylidene)arylamines" retrieved from STN Database accession No. 99:139477 XP002267366 Zusammenfassung -& JP 58 099454 A (Sumitomo Chemical Co., Ltd., Japan) Jun. 13, 1983.

Misra, Vinay S. et al: "Possible antituberculous compds. IX. Prepn. on benzylidene and benzyl derivs. of 4-aminodiphenylamine" J. Indian Chem. Soc. (1960), 37, 481-2, XP008025987 Seite 482, Tabelle I, S. No. 9.

Barmettler, Peter et al: "Acid-catalyzed '3, 3! -sigmatropic rearrangements of N-propargylanilines" Helvetica Chimica Acta (1990), 73(6), 1515-73, XP008026042 Seite 1518: Verbindungen 16-19; Seite 1540: Verbindung 104.

Al-Dilaimi, Sobhi K. et al: "Apparent stability constants and thermodynamic functions of Cinnamylideneaniline Schiff base complexes with aluminum chloride" Thermochimica Acta (1986), 97, 267-70, XP008026038, Seite 268, Tabelle 1.

* cited by examiner

*Primary Examiner*—Robert D. Harlan
(74) *Attorney, Agent, or Firm*—Nicanor A. Kohncke; Jennifer R. Seng

(57) ABSTRACT

The present invention relates to anti-aging agents based on organic compounds containing conjugated azadiene groups, which are capable of providing rubber vulcanizates with long-term protection against thermal aging, fatigue and aging as a result of the effects of oxygen. The anti-aging agents according to the present invention are further characterized in that they are hardly ever extracted from the vulcanizates by water, oils and/or gasolines or hydraulic fluids.

8 Claims, No Drawings

ANTI-AGING AGENTS FOR RUBBER VULCANIZATES BASED ON ORGANIC COMPOUNDS CONTAINING CONJUGATED AZADIENES

FIELD OF THE INVENTION

The present invention relates to anti-aging agents based on organic compounds containing conjugated azadiene groups, which are capable of providing rubber vulcanizates with long-term protection against, for example, thermal aging, fatigue and aging as a result of the effects of oxygen. The anti-aging agents according to the present invention are further characterized in that they are hardly ever extracted from the vulcanizates by water, oils and/or gasolines or hydraulic fluids.

BACKGROUND OF THE INVENTION

The protection of rubber vulcanizates from destructive environmental influences by means of anti-aging agents is known. Thus e.g. phenolic, aminic, sulfur-containing or phosphor-containing anti-aging agents are added to rubber vulcanizates to improve their heat-resistance and storage stability. An overview of known anti-aging agents for rubbers is disclosed, for example, in Ullmanns Enzyklopädie der technischen Chemie, Verlag Chemie, Weinheim, 4$^{th}$ edition (1974), volume 8, pp. 19-45.

Improved, co-vulcanizable anti-aging agents, which can be produced by reacting optionally substituted p-phenylenediamines and/or sterically hindered phenols with bifunctional alkyl-, aryl- and/or aralkyl compounds and subsequently reacting the product thus obtained with sulfur and/or sulfur-yielding compounds, are disclosed in co-pending U.S. patent application Ser. No. 09/850,511.

Co-pending U.S. patent application Ser. No. 09/850,511 discloses known anti-aging agents for rubber vulcanizates, although it should be pointed out that the known anti-aging agents have considerable disadvantages because of their ready volatility or extractability. The co-vulcanizable anti-aging agents disclosed in co-pending U.S. patent application Ser. No. 09/850,511 avoid these disadvantages.

However, to produce the anti-aging agents disclosed therein, a relatively complex, two-stage synthesis is required, which comprises the reaction of, for example, phenylenediamines with difunctional alkyl-, aryl- or aralkyl compounds with subsequent reaction of the products obtained in this reaction with sulfur and/or sulfur-yielding compounds.

An object of the present invention is therefore to provide an anti-aging agent that can be produced in a simple, single-stage synthesis and avoids the disadvantages of the known anti-aging agents already mentioned in co-pending U.S. patent application Ser. No. 09/850,511, such as volatility and extractability, without reducing the effectiveness of the anti-aging agent according to the present invention in comparison with the anti-aging agents previously known.

SUMMARY OF THE INVENTION

The present invention provides anti-aging agents for rubber vulcanizates, based on organic compounds containing conjugated azadiene groups of the general formula (I)

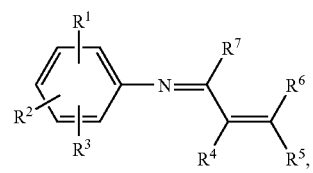

in which $R^1$ represents hydrogen, straight-chain or branched $C_1$-$C_{12}$-alkyl, $C_1$-$C_{12}$-alkoxy-, $C_1$-$C_{12}$-alkylthio-, $C_1$-$C_{12}$-alkylamino, di-($C_1$-$C_{12}$-alkyl)-amino-, $C_6$-$C_{14}$-aryl-, $C_6$-$C_{14}$-aryloxy-, $C_6$-$C_{14}$-arylthio-, $C_6$-$C_{14}$-arylamino, $C_2$-$C_{12}$-heteroaryl-, $C_2$-$C_{12}$-heteroaryloxy-, $C_2$-$C_{12}$-heteroarylthio-, $C_2$-$C_{12}$-heteroarylamino, $R^2$ and $R^3$ are the same or different and represent hydrogen, straight-chain or branched $C_1$-$C_{12}$-alkyl, $C_1$-$C_{12}$-alkoxy-, $C_1$-$C_{12}$-alkylthio-, $C_1$-$C_{12}$-alkylamino, di-($C_1$-$C_{12}$-alkyl)-amino-, benzyl-, 1,1-dimethylbenzyl- or phenyl- or together form a 5-10-link, aliphatic or aromatic, mono- or polynuclear ring system, which may optionally be interrupted once or more than once by heteroatoms, such as N, O or S, $R^4$ to $R^7$ are the same or different and represent hydrogen, straight-chain or branched $C_1$-$C_{12}$-alkyl-, $C_5$-$C_{12}$-cycloalkyl- or $C_6$-$C_{14}$-aryl-, mono- or polyunsaturated, olefinic or acetylenic, straight-chain or branched $C_2$-$C_{12}$-alkenyl-, $C_2$-$C_{12}$-alkinyl- or $C_5$-$C_8$-cycloalkenyl, or together form a 5-8-link aliphatic ring system, which may optionally be interrupted once or more than once by heteroatoms, such as N, O or S.

DETAILED DESCRIPTION OF THE INVENTION $C_1$-$C_{12}$-alkyl is understood to mean all linear, cyclic, or branched alkyl groups having 1 to 12 C atoms known to the person skilled in the art, such as methyl, ethyl, n-propyl, i-propyl, n-butyl, i-butyl, t-butyl, n-pentyl, i-pentyl, neopentyl, n-hexyl, cyclohexyl, i-hexyl, heptyl, octyl, nonyl, decyl, undecyl and dodecyl, which, in turn, may themselves be substituted.

Halogen-, nitro-, hydroxyl- and also $C_1$-$C_{12}$-alkyl- or alkoxy- and $C_6$-$C_{12}$-cycloalkyl- or aryl- are possible substituents here, as are benzoyl-, trimethylphenyl-, ethylphenyl-, chloromethyl-, chloroethyl- and nitromethyl-.

$C_1$-$C_{12}$-alkoxy- is understood to mean all linear or branched alkoxy groups having 1 to 12 C atoms known to the person skilled in the art, such as methoxy, ethoxy, n-propoxy, i-propoxy, n-butoxy, i-butoxy, t-butoxy, n-pentoxy, i-pentoxy, neo-pentoxy and hexoxy, which, in turn, may themselves be substituted by the substituents mentioned above.

$C_1$-$C_{12}$-alkylamino- is understood to mean all linear, branched, straight-chain or cyclic alkylamino groups having 1 to 12 C atoms, known to the person skilled in the art, such as methylamino-, ethylamino-, n-propylamino-, i-propylamino-, n-butylamino-, i-butylamino-, t-butylamino-, n-pentylamino-, i-pentylamino-, neo-pentylamino-, hexylamino-, cyclohexylamino- which, in turn, may themselves be substituted by the substituents mentioned above.

$C_1$-$C_{12}$-dialkylamino- is understood to mean all linear, branched, straight-chain or cyclic dialkylamino groups having 1 to 12 C atoms, known to the person skilled in the art, such as dimethylamino-, diethylamino-, methylethylamino-, methyl-isopropylamino-, methyl-tert.-butylamino-, dicyclohexylamino-, which, in turn, may themselves be substituted by the substituents mentioned above.

$C_1$-$C_{12}$-alkylthio- is understood to mean all linear or branched alkylthiyl groups having 1 to 12 C atoms known to the person skilled in the art, such as methylthio-, ethylthio-, n-propylthio-, i-propylthio-, n-butylthio-, i-butylthio-, t-butylthio-, n-pentylthio-, i-pentylthio-, neo-pentylthio- or hexylthio-, which, in turn, may themselves be substituted by the substituents mentioned above.

$C_5$-$C_{12}$-cycloalkyl- is understood to mean all mono- or polynuclear cycloalkyl groups having 5 to 12 C atoms known to the person skilled in the art, such as cyclopentyl-, cyclohexyl-, cycloheptyl-, cyclooctyl- and cyclononyl-, which, in turn, may themselves be substituted. Halogen-, nitro-, hydroxyl- and also $C_1$-$C_{12}$-alkyl- or alkoxyl- as well as $C_6$-$C_{12}$-cycloalkyl- or aryl- are possible substitutents here, as are methylcyclohexyl-, chlorocyclohexyl- and nitrocyclohexyl-.

$C_6$-$C_{14}$-aryl- is understood to mean all mono- or polynuclear aryl groups having 6 to 14 C atoms known to the person skilled in the art, such as phenyl-, naphthyl-, anthracenyl-, which, in turn, may themselves be substituted. Halogen-, nitro-, hydroxyl-, and also $C_1$-$C_{12}$-alkyl- or alkoxyl-, as well as $C_6$-$C_{12}$-cycloalkyl- or aryl- are possible substituents here, as are bromophenyl-, chlorophenyl-, toluyl- and nitrophenyl-.

$C_6$-$C_{14}$-aryloxy- is understood to mean all mono- or polynuclear oxy-aryl groups known to the person skilled in the art, in which the oxygen radical is substituted by one of the $C_6$-$C_{14}$ aryl groups mentioned above.

$C_6$-$C_{14}$-arylamino is understood to mean all mono- or polynuclear amino-aryl groups known to the person skilled in the art, in which the nitrogen radical is substituted by a hydrogen atom and one of the $C_6$-$C_{14}$-aryl groups mentioned above.

$C_6$-$C_{14}$-arylthio- is understood to mean all mono- or polynuclear thio-aryl groups known to the person skilled in the art, in which the sulfur radical is substituted by one of the $C_6$-$C_{14}$-aryl-groups mentioned above.

$C_2$-$C_{12}$-heteroaryl- is understood to mean all mono- or polynuclear heteroaryl groups known to the person skilled in the art, which contain in addition to 2 to 12 C atoms, heteroatoms such as N and/or O and/or S, in the aromatic ring system, such as e.g. pyridinyl-, triazinyl-, furyl-, thienyl-, thiazolyl-, thiazinyl-, pyrrolyl-, quinolinyl-, which, in turn, may themselves be substituted by the substituents mentioned above.

$C_6$-$C_{12}$-heteroaryloxy- is understood to mean all mono- or polynuclear oxy-heteroaryl groups known to the person skilled in the art, in which the oxygen radical is substituted by one of the $C_6$-$C_{14}$-heteroaryl groups mentioned above.

$C_6$-$C_{14}$-heteroarylamino- is understood to mean all mono- or polynuclear amino-heteroaryl groups known to the person skilled in the art, in which the nitrogen radical is substituted by a hydrogen atom and one of the $C_6$-$C_{14}$ heteroaryl groups mentioned above.

$C_6$-$C_{12}$-heteroarylthio is understood to mean all mono- or polynuclear thio-heteroaryl groups known to the person skilled in the art, in which the sulfur radical is substituted by one of the $C_6$-$C_{14}$-heteroaryl groups mentioned above.

The following are possible 5- to 10-ring aliphatic or aromatic, mono- or polynuclear ring systems that may be formed by groups $R^2$ and $R^3$ together and that may be interrupted once or more than once by heteroatoms:

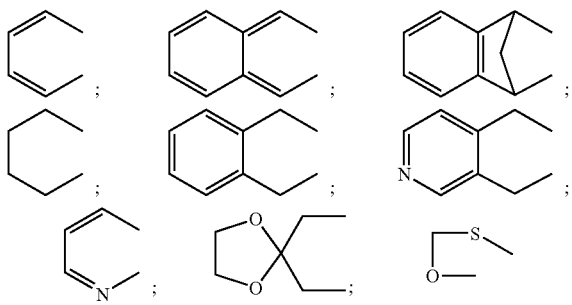

Mono- or polyunsaturated, olefinic or acetylenic, straight-chain or branched $C_2$-$C_{12}$-alkenyl-, $C_2$-$C_{12}$-alkinyl- or $C_5$-$C_8$-cycloalkenyl are understood to mean all related groups known to the person skilled in the art such as vinyl, ethinyl, buta-1,3-dienyl, propinyl, 2-methylbuta-1,3-dienyl, cyclopentenyl, cyclohexenyl and cyclooctadienyl, which, in turn, may themselves be substituted by the substituents mentioned above.

Hydrogen, methyl, ethyl, propyl, t-butyl, 2-propyl, 2-butyl, methoxy, ethoxy, butoxy, propoxy, hexyloxy, cyclohexyl, benzoyl, phenyl, naphthyl, chlorophenyl, tolyl, methylamino, ethylamino, propylamino, 2-propylamino, 2-butylamino, ethylamino, cyclohexylamino, phenylamino, naphthylamino, chlorophenylamino and tolylamino are preferred as groups $R^1$ to $R^3$.

Hydrogen, methyl, ethyl, propyl, butyl, isopropyl, 2-butyl, phenyl, benzyl, naphthyl, cyclohexyl, cyclohexenyl, vinyl, ethinyl, buta-1,3-dienyl and propinyl are preferred as groups $R^4$ to $R^7$.

Those of the following formulae include preferred organic compounds containing conjugated azadiene groups:

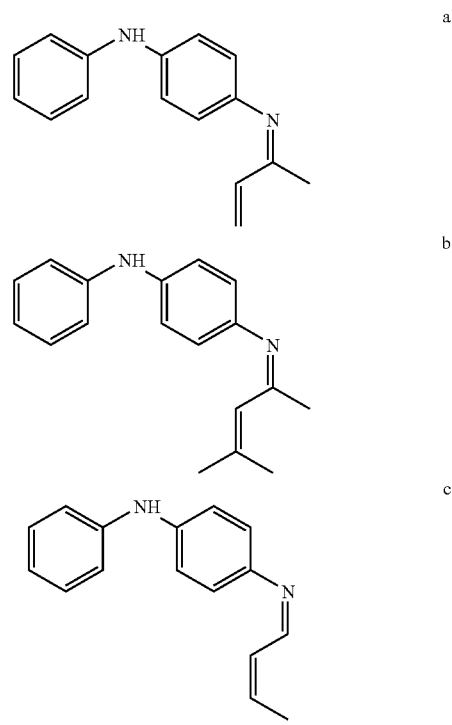

-continued

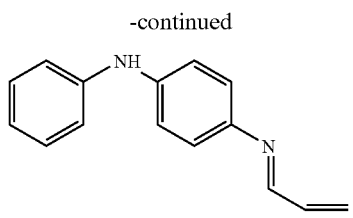
d

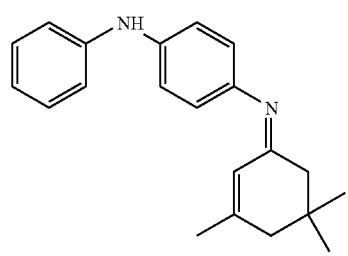
e

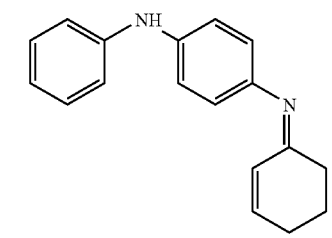
f

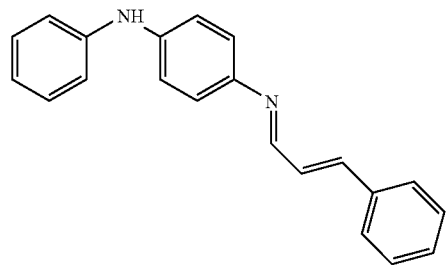
g (a) 1-N-(4'-N'-phenylamino-1'-phenyl)-2-methyl-1-azabuta-1,3-diene,
(b) 1-N-(4'-N'-phenylamino-1'-phenyl)-2,4-dimethyl-1-azapenta-1,3-diene
(c) 1-N-(4'-N'-phenylamino-1'-phenyl)-1-azapenta-1,3-diene,
(d) 1-N-(4'-N'-phenylamino-1'-phenyl)-1-azabuta-1,3-diene,
(e) 1-N-(4'-N'-phenylamino-1'-phenyl)-3,5,5-trimethyl-1-azamethylenecyclohex-2-ene,
(f) 1-N-(4'-N'-phenylamino-1'-phenyl)-1-azamethylenecyclohex-2-ene,
(g) 1-N-(4'-N'-phenylamino-1'-phenyl)-4-phenyl-1-azabuta-1,3-diene.

The anti-aging agents according to the present invention can be produced by reacting optionally substituted, primary aromatic amines and optionally substituted conjugated 1,3-enones and/or 1,3-enals and/or their synthetic equivalents, such as their hemi-acetal, acetal, aminal, aza- or thiocarbonyl derivatives.

Those of the formula (II)

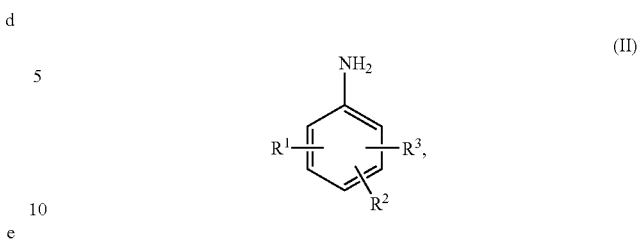

containing the groups $R^1$ to $R^3$ given above are possible optionally substituted primary aromatic amines.

Those of the formula (III)

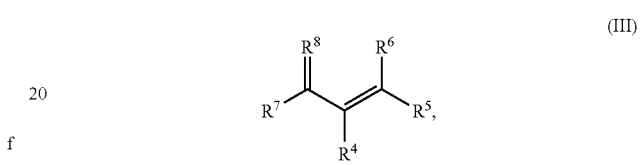

in which groups $R^4$ to $R^7$ have the meaning given above and $R^8$ stands for oxygen, sulfur, or the $NR^4$ group, having the meaning given above for $R^4$, are possible optionally substituted conjugated 1,3-enones and/or 1,3-enals.

Those of the formula (IV)

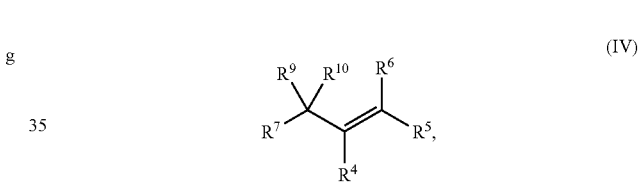

in which
$R^4$ to $R^7$ have the meaning given above and
$R^9$ and $R^{10}$ are the same or different and stand for hydroxy, chloro, bromo, straight-chain or branched $C_1$-$C_{12}$-alkoxy, $C_1$-$C_{12}$-alkylthio, $C_1$-$C_{12}$-alkylamino or together form a $C_2$-$C_{12}$-alkanedioxy- or $C_2$-$C_{12}$-alkanediamino group, are possible optionally substituted synthetic equivalents (i.e. compounds which, under the reaction conditions, react in the same way as the corresponding 1,3-enones or 1,3-enals) of conjugated 1,3-enones and/or 1,3-enals.

Useful aromatic amines include, 4-alkoxy-anilines, such as e.g. 4-hexyloxy-aniline, 4-ethoxy-aniline, 4-methoxy-aniline, 4-butoxy-aniline, 4-propoxy-aniline, 4-(2'-ethylhexyl)oxy-aniline, 4-hydroxyaniline, N-phenyl-4-phenylenediamine, alkylated para-phenylenediamines such as e.g. N-(2'-methyl-phenyl)-4-phenylenediamine, N-(2'-ethyl-phenyl)-4-phenylenediamine, N-(4'-methyl-phenyl)-4-phenylenediamine, N-(4'-ethyl-phenyl)-4-phenylenediamine, N-(2'-methoxy-phenyl)-4-phenylenediamine, N-(2'-ethoxy-phenyl)-4-phenylene diamine, N-(4'-methoxy-phenyl)-4-phenylene-diamine, N-(4'-ethoxy-phenyl)-4-phenylenediamine, 6-ethoxyquinoline, 1-naphthylamine, 2-naphthylamine.

The mono- or polyunsaturated carbaldehydes and/or ketones of the formula (III) are useful for the production of the anti-aging agent according to the present invention include, cyclopent-2-en-1-one, cyclohex-2-en-1-one, cyclohept-2-en-1-one, 2-methylpent-2-en-4-one, pent-3-in-2-one, 2,6-dimethylhepta-2,5-dien-4-one, prop-1-en-3-al, but-1-en-3-one, but-3-en-1-al, 3,5,5-trimethylcyclohex-2-en-1-one, 3-phenylprop-2-enal.

Preferred conjugated ketones and aldehydes include, 2-methylpent-2-en-4-one, 2,6-dimethylhepta-2,5-dien-4-one, but-1-en-3-one, 3,5,5-trimethylcyclohex-2-en-1-one, prop-2-en-1-al.

The following derivatives of mono- or polyunsaturated carbaldehydes and/or ketones of the formula (IV) for example are useful in the production of the anti-aging agents according to the present invention, 2-methylpent-2-en-4-thione, 2,6-dimethylhepta-2,5-dien-4-thione, but-1-en-3-thione, 3,5,5-trimethylcyclohex-2-en-1-thione, 2-methylpent-2-en-4-imine, 2,6-dimethylhepta-2,5-dien-4-imine, but-1-en-3-imine, 3,5,5-trimethylcyclohex-2-en-1-imine, 2,2-dimethoxypent-3-ene, 3,3-dimethoxybutene, 2,2-dimethoxy-4-methylpent-3-ene, 2,2-ethylenedioxypent-3-ene, 3,3-ethylenedioxybutene, 2,2-ethylenedioxy-4-methylpent-3-ene, 4,4-dimethoxy-2,6-dimethylhepta-2,5-diene, 4,4-ethylenedioxy-2,6-dimethylhepta-2,5-diene, 4,4-diethoxy-2,6-dimethylhepta-2,5-diene, 1,1-dimethoxyprop-2-ene, 1,1-dimethoxyprop-2-ine, 2,2-dimethoxybut-3-ene, 2,2-dimethoxybut-3-ine, 1,1-ethylenedioxyprop-3-ene, 1,1-dimethoxy-3,5,5-trimethylcyclohex-2-ene, 1,1-diethoxy-3,5,5-trimethylcyclohex-2-ene, 1,1-ethylenedioxy-3,5,5-trimethylcyclohex-2-ene, 1,1-dimethoxy-cyclohex-2-ene, 1,1-diethoxy-cyclohex-2-ene, 1,1-ethylenedioxy-cyclohex-2-ene.

The above-mentioned, optionally substituted compounds can of course also be used in mixture with each other.

As mentioned before, the substituted aromatic amines and the substituted p-phenylenediamines can be used in mixture with each other. The preferred mix ratio can easily be determined by preliminary tests and is based for example on the required physical properties of the anti-aging agent. The same applies to the mixture of optionally substituted conjugated ketones and/or aldehydes and/or their derivatives such as e.g. acetals, which can optionally be used.

The reaction of the aromatic amines and/or p-phenylenediamines with the optionally substituted conjugated ketones and/or aldehydes and/or their derivatives such as e.g. acetals, is carried out in the presence of inert, organic solvents.

The following, for example, are useful inert organic solvents that includealiphatic or aromatic hydrocarbons, which may optionally be substituted with alkyl-, alkoxy-, halogen-, nitro-, amino-, sulfo groups, and also aliphatic or aromatic ethers, amines and sulfides.

The preferred solvents include,alkyl benzenes, toluene, xylene, cymol, gasolines, chlorobenzene, dichlorobenzene, chlorotoluene.

The reaction mentioned above can, of course, be carried out without solvent, for example in an excess of conjugated ketones and/or aldehydes and/or their derivatives present in liquid form.

The preferred quantity of solvent to be used can easily be determined by suitable preliminary tests.

The reaction for the production of the anti-aging agent according to the present invention is normally carried out at temperatures of 30° C. to 300° C., preferably at 120 to 220° C., more preferably at 150 to 200° C.

The production of the anti-aging agent according to the present invention by the reactions described above may, of course, be accelerated by suitable catalysts. The following, for example, are useful catalysts:

Lewis acids, such as e.g. aluminium-, zinc-, tin-, titanium-, iron or boron halides, Bronstedt acids such as e.g. sulfuric- and sulfonic acids, hydrochloric acid, phosphoric acid and also the catalysts disclosed in DE 29 01 863 A1, such as $CaHPO_4$ and hydroxylapatite.

The catalysts are used in the conventional quantities (0.1 to 10 mol. %) in relation to one mol of aromatic amine.

The anti-aging agents according to the present invention may of course also be used in combination with known anti-aging agents in rubber vulcanizates.

Examples of such anti-aging agents include N-isopropyl-N'-phenyl-p-phenylenediamine, N-(1,3-dimethylbutyl)-N'-phenyl-p-phenylenediamine, N-1-isopropylidene-N'-phenyl-p-phenylenediamine, N-(1,3-dimethyl-1-butylidene)-N'-phenyl-p-phenylenediamine, N,N'-di(1,4-dimethylpentyl)-p-phenylenediamine, phenyl-1-naphthylamine, octylated diphenylamine, 2,2'-methylene-bis-(4-methyl-6-tert.-butyl-phenol) and 2,2,4-trimethyl-1,2-dihydroquinoline (monomeric and/or oligomerised and/or polymerised), in particular N-isopropyl-N'-phenyl-p-phenylenediamine, N-(1,3-dimethylbutyl)-N'-phenyl-p-phenylenediamine and N,N'-di(1,4-dimethylpentyl)-p-phenylenediamine, as well as mixtures of these with each other.

The preferred mix ratio can easily be determined by suitable preliminary tests and is based on the particular application of the vulcanizate to be protected. The ratio of the anti-aging agent according to the present invention to the known anti-aging agent in the mix is normally 10:1 to 1:10, preferably 5:1 to 1:2.

In addition, it is possible to mix the anti-aging agents according to the present invention with known ozone protection agents to obtain improved ozone protection of the rubber vulcanizates. Here too, the person skilled in the art can easily determine the preferred mix ratio, depending on the application of the rubber vulcanizate, by means of preliminary tests. The ozone protection agents are normally added to the anti-aging agents according to the present invention in quantities of 10:1 to 1:10, preferably 3:1 to 1:2, in relation to the anti-aging agent according to the present invention. The following ozone protection agents can be used in particular: N-isopropyl-N'-phenyl-p-phenylenediamine, N,N'-di(1,4-dimethylpentyl)-p-phenylenediamine, as well as the compounds listed in detail in D. Brück, Kautschuk, Gummi, Kunststoffe, 9 (1989) 760-770.

The anti-aging agents according to the present invention are normally used in quantities of 0.5 wt. % to 10 wt. %, preferably 1 wt. % to 5 wt. % in relation to 100 parts of the rubber used.

The rubber mix may, of course, contain other rubber auxiliary products such as reaction accelerators, heat stabilisers, light protection agents, processing auxiliary agents, plasticisers, tackifiers, blowing agents, dyes, pigments, waxes, extenders, organic acids, inhibitors, metal oxides and activators such as triethanol amine, polyethylene glycol, hexane triol, which are known and common in the rubber industry. The rubber auxiliary agents are added in conventional quantities according to the intended application. Conventional quantities are, for example, quantities of 0.1 to 50 wt. % in relation to the total quantity of rubber used.

In addition to the auxiliary products mentioned above, the known crosslinkers may be added to the rubber mixes, such as sulfur or sulfur-providers and vulcanization accelerators, such as mercaptobenzthiazols, benzthiazolsulfenamides, guanidines, thiurams, dithiocarbamates, thioureas and/or thiocarbonates. The vulcanization accelerators and the stated crosslinkers are normally used in quantities of 0.1 to 10 wt. %, preferably 0.1 to 5 wt. %, in relation to the total quantity of the rubber used in each case.

The vulcanization of the rubber mixes containing the anti-aging agents according to the present invention, can take place at conventional temperatures of 100 to 200° C., preferably 130 to 180° C. (optionally under 10 to 300 bar pressure).

The further mixing of the rubbers with the other stated rubber auxiliary products, crosslinkers and accelerators may be carried out in the conventional way with the aid of suitable mixing apparatus, such as rollers, internal mixers and mixer extruders.

The rubber mixes obtained may optionally be compounded and vulcanized in the conventional way, as disclosed in more detail for example in Encyclopedia of Polymer Science and Engineering, Vol. 4, p. 66 ff (Compounding) and Vol. 17 p. 666 ff (Vulcanisation).

The invention is further illustrated but is not intended to be limited by the following examples in which all parts and percentages are by weight unless otherwise specified.

EXAMPLES

Production of the anti-aging agents according to the invention

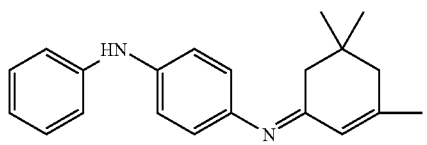

Compound A 184 g (1 mol) 4-ADPA (4-aminodiphenylamine) in 600 ml xylene was dissolved while stirring in a 1 l four-neck flask with water separator and thermometer and refluxed with 2 g p-toluene sulfonic acid. 179.7 g (1.3 mol) isophorone was dosed in. Within 8 hours 16.5 ml water separated out. 500 ml water and 50 g NaHCO$_3$ were then added to the reaction mixture, stirred, the phases were separated in the separating funnel and the organic phase was filtered through 50 g Na$_2$SO$_4$. After distillation (0.2 mbar, 100° C.) of the volatile portions, the raw product (brownish-black residue) was recrystallised from 600 ml toluene and 300 ml n-hexane. Yield: 99 g yellow, crystalline N-phenyl-N'-3,3,5-trimethyl-cyclohex-2-enylene-p-phenylenediamine, Fp.: 126-128° C.

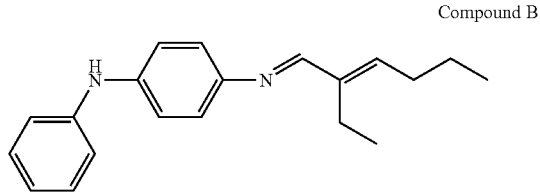

Compound B 4-(2'-ethylhex-2'-enyl-1'-imino)-diphenylamine 184 g (1 mol) 4-aminodiphenylamine (4-APDA), 4 g glacial acetic acid as a catalyst and 600 ml toluene were provided in a nitrogen atmosphere in a 2 l four-neck flask with water separator, thermometer and KPG stirrer, and were refluxed. At this temperature, 163.8 g (1.3 mol) 2-ethylhex-2-enal was dropped in slowly, while stirring, within six hours, 17.8 ml reaction water being formed and removed with the water separator. The mixture was stirred for a further three hours at the same temperature, until a thin layer test indicated the complete consumption of 4-ADPA. After cooling to room temperature, a solution of 3 g NaOH in 100 ml water was added to neutralise the acid. The phases were separated in a separating funnel. The solvent was removed in a water jet vacuum and the residue distilled through a short Vigreux column (220° C., 1 mbar). 283 g of a brownish-black oil is obtained as a distillate, which was characterized by GC/MS. GC/MS: Isomer mixture, 85% pure, m/z: 292(m+), 277, 263, 249, 234, 184, 183 (100%), 167.

TABLE 1

| Masterbatch formulation | |
|---|---|
| Masterbatch | |
| TSR 5[a] | 100 phr |
| Corax N 339[b] | 55 |
| Enerthene 1849-1[c] | 3 |
| Stearic acid[d] | 2.5 |
| Zinc white RS[e] | 5 |
| Antilux 111[f] | 1 |
| | 166.5 |

TABLE 2

| Vulcanized Rubber Mixture | | | | |
|---|---|---|---|---|
| Masterbatch | 166.5 | 166.5 | 166.5 | 166.5 |
| Without AAA | — | — | — | — |
| Vulkanox 4020 | — | 2 | — | — |
| Compound A | — | — | 2 | — |
| Compound B | — | — | — | 2 |
| Roller: | | | | |
| Rhenocure IS-90-20[f] | 1.8 | 1.8 | 1.8 | 1.8 |
| Vulkacit CZ[g] | 1.5 | 1.5 | 1.5 | 1.5 |

TABLE 3

| Properties (Rheometer: MDR 2000, DIN 53529, 150° C., 60 min.) | | | | |
|---|---|---|---|---|
| | Without AAA | Vulkanox 4020 | Compound A | Compound B |
| ts 02 [min.] | 3.4 | 3.0 | 1.0 | 1.6 |
| t 90 [min.] | 7.1 | 6.2 | 2.6 | 3.3 |

| | |
|---|---|
| a) | Available from Weber & Schaer GmbH & Co, Hamburg |
| b) | Available from Deutsche Gasrußwerke GmbH, Dortmund |
| c) | Available from BP Schmierstoff GmbH, Hamburg |
| d) | Available from Henkel KGaA, Dehydag, Oleogrundstoffe, Dusseldorf |
| e) | Available from Grillo Zinkoxid GmbH, Goslar |
| f) | Available from Rhein Chemie Rheinau GmbH, Mannheim |
| g) | Available from Bayer AG, Leverkusen |

The rubber mixes were produced as follows:

All listed substances, see Table 1, except sulfur and Vulkacit® CZ were mixed into the rubber matrix in a TPE kneader GK 1.5 E (volume ca 1500 ml), temperature=40° C. Sulfur (Rhenocure 95-2) and Vulkacit® CZ were then incorporated into the mix on a roller (150 mm Ø) at 40° C., see Table 2. The speed of the rollers was 12 rpm at a friction of 1.22.

The mixes were then vulcanized to rubber sheets (100× 100×2 mm) in electric heated presses (300 bar) at 150° C. to $t_{90}$+5 min. of the rheometer curves.

The mechanical-dynamic properties of the vulcanizates were tested under various conditions:
1. when fresh
2. after seven days' hot air aging at 70° C.
3. after 14 days' hot air aging
4. after extraction with acid water at pH4 and 80° C.

The results appear in Table 3. The hot air aging of the test bodies is intended to simulate the normal aging process of rubber articles in a shorter time and is well known to the person skilled in the art for this purpose.

Extraction in acid water at pH 4 in these tests is intended to simulate the effects of acid rainwater, for example, and to dissolve the aminic anti-aging agents out of the test body under intensified conditions.

Extraction was effected by immersing the sample bodies in temperature-controlled (80° C.) aqueous buffer solutions. The extraction medium was renewed daily.

As a reference, test bodies were also tested, which contained no anti-aging agent (without AAA) and those protected against the aging process by Vulkanox® 4020 (6-PPD), the prior art.

The mechanical-dynamic properties, e.g. modulus [M], tensile strength [TS] and elongation at break [EB] of the vulcanizates are given in Tables 4-6.

TABLE 4

Tensile tests to DIN 53504, Standard bar S 2 at 20° C.

| Freshly vulcanised test bodies | | Without AAA | Vulkanox 4020 | Compound A | Compound B |
|---|---|---|---|---|---|
| M 100 [%] | MPa | 3.1 | 3.0 | 2.3 | 2.7 |
| M 300 [%] | MPa | 16.4 | 16.1 | 12.5 | 13.6 |
| TS | MPa | 28.7 | 29.6 | 29.5 | 28.7 |
| EB | % | 492 | 507 | 600 | 553 |

TABLE 5a

Aging without extraction

| 7 days' hot air aging 70° C. | | Without AAA | 4020 | Compound A | Compound B |
|---|---|---|---|---|---|
| M 100 [%] | MPa | 3.7 | 3.8 | 3.2 | 3.9 |
| M 300 [%] | MPa | 17.6 | 18.5 | 16.0 | 18.1 |
| TS | MPa | 22.7 | 26.5 | 27.8 | 28.0 |
| EB | % | 383 | 437 | 504 | 482 |

TABLE 5b

Aging without extraction

| 14 days' hot air aging, 70° C. | | Without AAA | 4020 | Compound A | Compound B |
|---|---|---|---|---|---|
| M 100 [%] | MPa | 4.3 | 4.4 | 3.4 | 4.0 |
| M 300 [%] | MPa | 19.2 | 20.3 | 15.8 | 17.1 |
| TS | MPa | 23.7 | 29.1 | 26.5 | 26.7 |
| EB | % | 371 | 424 | 488 | 442 |

TABLE 6

After Extraction in water, 80° C., pH 4

| 7 days' extraction | | Without AAA | 4020 | Compound A | Compound B |
|---|---|---|---|---|---|
| M 100 [%] | MPa | 3.8 | 3.9 | 3.2 | 3.6 |
| M 300 [%] | MPa | 20.0 | 21.3 | 15.8 | 17.1 |
| TS | MPa | 23.9 | 28.1 | 27.8 | 25.9 |
| EB | % | 347 | 378 | 504 | 482 |

Results of the Test Series:

These tests showed that compounds A and B according to the present invention already have better elongation at break in the mechanical properties of the fresh, un-aged and unextracted test bodies than the standard (600% for A or 553% for B as against 507% for Vulkanox® 4020) and to that extent are capable of providing rubber articles with better protection against aging influences.

This result was also repeated after seven and fourteen days' hot air aging at 70° C.

The difference from the standard after storage of the test bodies under extractive conditions in acid water is even more striking. The rubber bodies protected with Vulkanox® 4020 achieved an elongation at break of only 378%, while protection by the compounds according to the present invention permits values for elongation at break of 504% (A) and 482% (B).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for reducing the aging characteristics of a rubber vulcanizate comprising admixing an anti-aging agent having the formula (I)

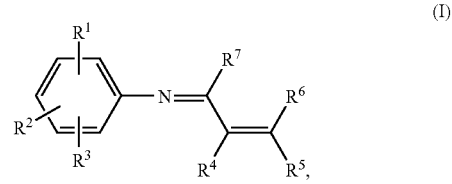

(I)

wherein
R$^1$ represents hydrogen, straight-chain or branched C$_1$-C$_{12}$-alkyl, C$_1$-C$_{12}$-alkoxy-, C$_1$-C$_{12}$-alkylthio-, C$_1$-C$_{12}$-alkylamino, di-(C$_1$-C$_{12}$-alkyl)-amino-, C$_6$-C$_{14}$-aryl-, C$_6$-C$_{14}$-aryloxy-, C$_6$-C$_{14}$-arylthio-, C$_6$-C$_{14}$-arylamino, C$_2$-C$_{12}$-heteroaryl-, C$_2$-C$_{12}$-heteroaryloxy-, C$_2$-C$_{12}$-heteroarylthio-, C$_2$-C$_{12}$-heteroarylamino, R$^2$ and R$^3$ are the same or different and represent straight-chain or branched C$_1$-C$_{12}$-alkyl, C$_1$-C$_{12}$-alkoxy-, C$_1$-C$_{12}$-alkylthio-, C$_1$-C$_{12}$-alkyl-amino, di-(C$_1$-C$_{12}$-alkyl)-amino-, benzyl-, 1,1-dimethylbenzyl- or phenyl-, or together form a 5-10-link aliphatic or aromatic, mono- or polynuclear ring system, which may optionally be interrupted once or more than once by heteroatoms selected from the group consisting of N, O and S, $R^4$ to $R^7$ are the same or different and represent hydrogen, straight-chain or branched $C_1$-$C_{12}$-alkyl-, $C_5$-$C_{12}$-cycloalkyl- or $C_6$-$C_{14}$-aryl-, mono- or polyunsaturated, olefinic or acetylenic, straight-chain or branched $C_2$-$C_{12}$-alkenyl-, $C_1$-$C_{12}$-alkinyl- or $C_5$-$C_8$-cycloakenyl, or together form a 5-8-link, aliphatic ring system, which may optionally be interrupted once or more than once by heteroatoms selected from the group consisting of N, O and S, with at least one rubber monomer and a vulcanizing agent.

2. The method according to claim 1, wherein the anti-aging agent is prepared by reacting substituted primary aromatic amines having the formula (II)

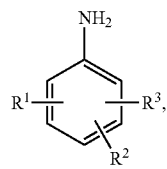
(II)

wherein, $R^1$ represents hydrogen, straight-chain or branched $C_1$-$C_{12}$-alkyl, $C_1$-$C_{12}$-alkoxy-, $C_1$-$C_{12}$-alkylthio-, $C_1$-$C_{12}$-alkylamino, di-($C_1$-$C_{12}$-alkyl)-amino-, $C_6$-$C_{14}$-aryl-, $C_6$-$C_{14}$-aryloxy-, $C_6$-$C_{14}$-arylthio-, $C_6$-$C_{14}$-arylamino-, $C_2$-$C_{12}$-heteroaryl-, $C_2$-$C_{12}$-heteroaryloxy-, $C_2$-$C_{12}$-heteroarylthio- and $C_2$-$C_{12}$-heteroarylamino, $R^2$ and $R^3$ are the same or different and represent straight-chain or branched $C_1$-$C_{12}$-alkyl, $C_1$-$C_{12}$-alkoxy-, $C_1$-$C_{12}$-alkylthio-, $C_1$-$C_{12}$-alkyl-amino, di-($C_1$-$C_{12}$-alkyl)-amino-, benzyl-, 1,1-dimethylbenzyl-, phenyl-, or together form a 5-10-link aliphatic or aromatic, mono- or polynuclear ring system, which may optionally be interrupted once or more than once by heteroatoms selected from the group consisting of N, O and S, with optionally substituted conjugated 1,3-enones and/or 1,3-enals having the formula (III)

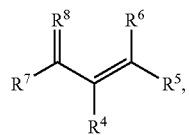
(III)

wherein, $R^4$ to $R^7$ are the same or different and represent of hydrogen, straight-chain or branched $C_1$-$C_{12}$-alkyl-, $C_5$-$C_{12}$-cycloalkyl or $C_6$-$C_{14}$-aryl-, mono- or polyunsaturated, olefinic or acetylenic, straight-chain or branched $C_2$-$C_{12}$-alkenyl-, $C_2$-$C_{12}$-alkinyl- or $C_5$-$C_8$-cycloakenyl, or together form a 5-8-link, aliphatic ring system, which may optionally be interrupted once or more than once by heteroatoms selected from the group consisting of N, O and S, and wherein $R^8$ represents oxygen, sulfur and $NR^4$ group and/or their synthetic equivalents having the formula (IV)

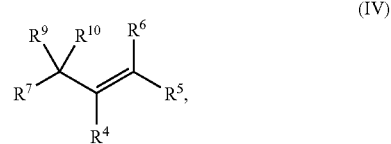
(IV)

wherein, $R^9$ and $R^{10}$ are the same or different and represent hydroxy, chloro, bromo, straight-chain or branched $C_1$-$C_{12}$-alkoxy, $C_1$-$C_{12}$-alkylthio, $C_1$-$C_{12}$-alkylamino or together form a $C_2$-$C_{12}$-alkanedioxy- or $C_2$-$C_{12}$-alkanediamino group.

3. The method according to claim 1 further comprising admixing least one additional anti-aging agent, wherein the mix ratio of anti-aging agents according to claim 1 to at least one additional anti-aging agent is 10:1 to 1:10.

4. A rubber mixture comprising at least one rubber monomer, at least one anti-aging agent and a vulcanizing agent, the anti-aging agent having the formula (I)

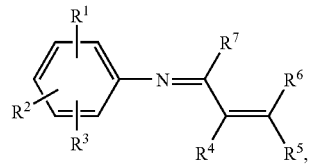
(I)

wherein $R^1$ represents hydrogen, straight-chain or branched $C_1$-$C_{12}$-alkyl, $C_1$-$C_{12}$-alkoxy-, $C_1$-$C_{12}$-alkylthio-, $C_1$-$C_{12}$-alkylamino, di-($C_1$-$C_{12}$-alkyl)-amino-, $C_6$-$C_{14}$-aryl-, $C_6$-$C_{14}$-aryloxy-, $C_6$-$C_{14}$-arylthio-, $C_6$-$C_{14}$-arylamino-, $C_2$-$C_{12}$-heteroaryl-, $C_2$-$C_{12}$-heteroaryloxy-, $C_2$-$C_{12}$-heteroarylthio-, $C_2$-$C_{12}$-heteroarylamino, $R^2$ and $R^3$ are the same or different and represent straight-chain or branched $C_1$-$C_{12}$-alkyl, $C_1$-$C_{12}$-alkoxy-, $C_1$-$C_{12}$-alkylthio-, $C_1$-$C_{12}$-alkyl-amino, di-($C_1$-$C_{12}$-alkyl)-amino-, benzyl-, 1,1-dimethylbenzyl- or phenyl-, or together form a 5-10-link aliphatic or aromatic, mono- or polynuclear ring system, which may optionally be interrupted once or more than once by heteroatoms selected from the group consisting of N, O and S, $R^4$ to $R^7$ are the same or different and represent hydrogen, straight-chain or branched $C_1$-$C_{12}$-alkyl-, $C_5$-$C_{12}$-cycloalkyl- or $C_6$-$C_{14}$-aryl-, mono- or polyunsaturated, olefinic or acetylenic, straight-chain or branched $C_2$-$C_{12}$-alkenyl-, $C_2$-$C_{12}$-alkinyl- or $C_5$-$C_8$-cycloakenyl, or together form a 5-8-link, aliphatic ring system, which may optionally be interrupted once or more than once by heteroatoms selected from the group consisting of N, O and S.

5. A process for preparing the rubber mixture according to claim 4, comprising mixing the at least one or more rubber monomer with the anti-aging agent and the vulcanizing agent.

6. The process according to claim 1, wherein the anti-aging agent is (a) 1-N-(4'-N'-phenylamino-1'-phenyl)-2-methyl-1-azabuta-1,3-diene, (b) 1-N-(4'-N'-phenylamino-1'- phenyl)-2,4-dimethyl-1-azapenta-1,3-diene, (c) 1-N-(4'-N'-phenylamino-1'-phenyl)-1-azapenta-1,3-diene, (d) 1-N-(4'-N'-phenylamino-1'-phenyl)-1-azabuta-1,3-diene, (e) 1-N-(4'-N'-phenylamino-1'-phenyl)-3,5,5-trimethyl-1-azamethylenecyclohex-2-ene, (f) 1-N-(4'-N'-phenylamino-1'-phenyl)-1-azamethylenecyclohex-2-ene, (g) 1-N-(4'-N'-phenylamino-1'-phenyl)-4-phenyl-1-azabuta-1,3-diene, or (h) combination thereof.

7. The rubber mixture according to claim 4, wherein the anti-aging agent is (a) 1-N-(4'-N'-phenylamino-1'-phenyl)-2-methyl-1-azabuta-1,3-diene, (b) 1-N-(4-N'-phenylamino-1'-phenyl)-2,4-dimethyl-1-azapenta-1,3-diene, (c) 1-N-(4'-N'-phenylamino-1'-phenyl)-1-azapenta-1,3-diene, (d) 1-N-(4'-N'-phenylamino-1'-phenyl)-1-azabuta-1,3-diene, (e) 1-N-(4'-N'-phenylamino-1'-phenyl)-3,5,5-trimethyl-1-azamethylenecyclohex-2-ene, (f) 1-N-(4'-N'-phenylamino-1'-phenyl)-1-azamethylenecyclohex-2-ene, (g) 1-N-(4'-N'-phenylamino-1'-phenyl)-4-phenyl-1-azabuta-1,3-diene, or (h) combination thereof.

8. The process according to claim 5, wherein the anti-aging agent is (a) 1-N-(4'-N'-phenylamino-1'-phenyl)-2-methyl-1-azabuta-1,3-diene, (b) 1-N-(4'-N'-phenylamino-1'-phenyl)-2,4-dimethyl-1-azapenta-1,3-diene, (c) 1-N-(4'-N'-phenylamino-1'-phenyl)-1-azapenta-1,3-diene, (d) 1-N-(4'-N'-phenylamino-1'-phenyl)-1-azabuta-1,3-diene, (e) 1-N-(4'-N'-phenylamino-1'-phenyl)-3,5,5-trimethyl-1-azamethylenecyclohex-2-ene, (f) 1-N-(4'-N'-phenylamino-1'-phenyl)-1-azamethylenecyclohex-2-ene, (g) 1-N-(4'-N'-phenylamino-1'-phenyl)-4-phenyl-1-azabuta-1,3-diene, or (h) combination thereof.

* * * * *